United States Patent
Prohaska et al.

(10) Patent No.: US 6,932,941 B2
(45) Date of Patent: Aug. 23, 2005

(54) METHOD AND APPARATUS FOR IMPROVED GAS DETECTION

(75) Inventors: Otto J. Prohaska, Seymour, CT (US); Avinash Dalmia, Hamden, CT (US); David Clark, Sandy Hook, CT (US)

(73) Assignee: PerkinElmer Instruments LLC, Shelton, CT (US)

( * ) Notice: Subject to any disclaimer, the term of this patent is extended or adjusted under 35 U.S.C. 154(b) by 52 days.

(21) Appl. No.: 10/397,757

(22) Filed: Mar. 26, 2003

(65) Prior Publication Data

US 2003/0164310 A1 Sep. 4, 2003

Related U.S. Application Data

(63) Continuation-in-part of application No. 09/443,875, filed on Nov. 19, 1999, now Pat. No. 6,682,638.

(51) Int. Cl.[7] .................................................. B01L 3/00
(52) U.S. Cl. ......................... 422/99; 422/83; 422/130; 422/54; 422/52; 422/98; 422/89; 436/123; 436/161; 436/172
(58) Field of Search .......................... 422/130, 98, 99, 422/89, 83, 54, 52, 100; 436/123, 161, 172; 204/409, 424

(56) References Cited

U.S. PATENT DOCUMENTS

| | | | |
|---|---|---|---|
| 4,038,053 A | 7/1977 | Golay | |
| 4,172,770 A | 10/1979 | Semersky et al. | |
| 4,812,221 A | 3/1989 | Madou et al. | |
| 4,820,386 A | 4/1989 | LaConti et al. | |
| 4,851,104 A | 7/1989 | Connery et al. | |
| 4,900,405 A | 2/1990 | Otagawa et al. | |
| 5,302,274 A | 4/1994 | Tomantschger et al. | |
| 5,331,310 A | 7/1994 | Stetter et al. | |
| 5,527,446 A | 6/1996 | Kosek et al. | |
| 5,545,252 A | 8/1996 | Hinshaw et al. | |
| 5,573,648 A | 11/1996 | Shen et al. | |
| 5,650,054 A | 7/1997 | Shen et al. | |
| 5,711,786 A | 1/1998 | Hinshaw | |
| 5,830,337 A | 11/1998 | Xu | |
| 5,889,197 A | 3/1999 | Van der Maas et al. | |
| 6,080,294 A | 6/2000 | Shen et al. | |
| 6,130,095 A | * 10/2000 | Shearer | 436/123 |
| 6,200,443 B1 | 3/2001 | Shen et al. | |
| 6,205,841 B1 | 3/2001 | Shibamoto | |
| 6,245,298 B1 | 6/2001 | Bremer et al. | |
| 6,338,823 B1 | 1/2002 | Furukawa | |
| 6,682,638 B1 | * 1/2004 | Prohaska et al. | 204/426 |

OTHER PUBLICATIONS

(Polyaniline thin–films for gas sensing), N.E. Agbor et al., 1995 Elsevier Science S.A. pp. 173–179.

(The Development of a Thick–Film Electrochemical Sensor and Instrumentation for In–Situ Determination of Carbon Dioxide Partial Pressure ($pCO_2$) In The Marine Environment), M.R. Creasey et al., University of Southampton, U.K., Electronic Engineering in Oceanography, Jul. 19–21, 1994, Conference Publication No. 394 IEE 1994.

(Sixth International Conference on Electronic Engineering in Oceanography) Electron theory of thin–film gas sensors, Helmut Geistlinger, 1993 Elsevier Sequoia, pp 47–60.

(Continued)

*Primary Examiner*—Jill Warden
(74) *Attorney, Agent, or Firm*—St. Onge Steward Johnston & Reens, LLc

(57) ABSTRACT

The invention relates to a method and apparatus for providing a reactor having a heater, a passage for transporting a reactant, and a chamber containing a gas sample and being coupled to the passage for receiving the reactant and mixing the reactant with the gas sample. The reactor further includes a connector leading from the chamber to the heater for transporting a mixture of the reactant and gas sample, and wherein the heater heats the mixture of the reactant and gas sample.

7 Claims, 7 Drawing Sheets

OTHER PUBLICATIONS (A Practical Reference Electrode) J. Giner, Pratt & Whitney Aircraft, Division of United Aircraft Corporation, East Hartford, CT.

(Design and application of thick–film multisensors) N. Hampp et al., 1992 Elsevier Sequoia pp. 144–148.

(Thin Film Porous Membranes for Catalytic Sensors) R.C. Hughes, et al., 1997 International Conference on Solid–State Sensors and Actuators Chicago, Jun. 16–19, 1997.

(Amperometric Gas Sensor of Thin Gold Film Electrode Ion–Plated on Gas Permeable Membrane for Detection of Arsine and Silane) Toru Ishiji et al., pp. 1019–1020.

(A solid–state pH sensor based on a Nafion–coated iridium oxide indicator electrode and a polymer–based silver chloride reference electrode) Patrick J. Kinlen et al., 1994 Elsevier Science pp 13–25.

(Multifunctional Sensors Based on Ceramic Electrolytes) Meilin Liu et al., Georgia Institute of Technology, Atlanta, Georgia pp 421–427.

(The thick–film route to selective gas sensors) F. Menil et al., 1995 Elsevier Science S.A. pp 415–420.

(Properties of vanadium oxide thin films for ethanol sensor) G. Micocci et al., J. Vac. Sci. Technol. A 15(1), Jan./Feb. 1997 American Vacuum Society.

(An Integrated Multi–Element Ultra–Thin–Film Gas Analyzer) N. Najuh et al., Solid–State Sensor and Actuator Workshop Proc. 5.

(Preparation of thin gold–film electrode for an electrochemical gas sensor for phosphine and arsine) Nobuo Nakano, et al., 1994 Elsevier Science S.A. pp 51–55.

(A Study of the Surface Sensitivity of Tin Oxide Sensors To Carbon Monoxide and Dioxide) Dario Narducci et al., Dept. of Physical Chemistry & Electrochemistry v. C. Golgi, 19 I–20133 Milano (Italy).

(UV–Polymerizable Screen–Printed Enzyme Pastes) Ingrid Rohm, et al., 1995 American Chemical Society Analyical Chemistry, vol. 67, No. 13, Jul. 1, 1995, Anal. Chem. 1995, 67, 2304–3207.

(CO–Sensor for domestic use based on high temperature stable $Ga_2O_3$ thin films), T. Schwebel, et al., 1997 International Conference on Solid–State Sensors and Actuators Chicago, Jun. 16–19, 1997.

(A Low–Power CMOS Compatible Integrated Gas Sensor Using Maskless Tin Oxide Sputtering) Lie–yi Sheng, et al., 1997 International Conference on Solid–State Sensors and Actuators Chicago, Jun. 16–19, 1997 pp 939–942.

(Platinum Thin Films and Next–Generation Micromachined Sensors) John Staley, et al., Sensors Apr. 1996.

(An amperometric carbon monoxide sensor based on the steady–state difference response technique) Y. Tan et al., 1995 Elsevier Science S.A. pp 113–121.

(A Novel Semiconductor No Gas Sensor Operating At Room Temperature) Zhang Wenyi et al., 1997 International Conference on Solid–State Sensors and Actuators, Chicago, Jun. 16–19, 1997.

(Environmental gas sensing) Noboru Yamazoe et al., 1994 Elsevier Science S.A. pp 95–102.

(Life–elongation mechanism of the polymer–electrolyte lamination on a CO sensor) Ayumu Yasuda, et al., 1994 Elsevier Science S.A. pp 229–236.

Carbon Monoxide Sensors, Beech et al., Electrochemistry at Loughborough, 1999.

* cited by examiner

US 6,932,941 B2

METHOD AND APPARATUS FOR IMPROVED GAS DETECTION

PRIORITY APPLICATION

This application is a continuation in part of U.S. patent application Ser. No. 09/443,875 for a "Film Type Solid Polymer Ionomer Sensor and Sensor Cell" filed on Nov. 19, 1999 now U.S. Pat. No. 6,682,638.

FIELD OF THE INVENTION

The invention relates to a method and apparatus for efficiently oxidizing and/or reducing a gas, resulting in an improved gas detection system.

BACKGROUND OF THE INVENTION

Gas detection, particularly detection of a specific gas component in a sample of gases, is traditionally achieved by introducing the gas sample into a gas detector, which often may be a mass spectrometer or electrolytic conductivity detector. Other detection systems may include thermal conductivity, flame ionization, and argon detectors.

Electrolytic conductivity detectors usually provide an electrical signal that is functionally related to the presence of a selected component and typically aid in determining properties of electrolytes in solutions. Such devices often include electrode surfaces with a continuous phase liquid electrolyte in between the electrode surfaces. These detectors generally entail measuring a difference in potential in the electrolytic material before and after the gas exiting the column enters the detector and is absorbed by the electrolytic material. If the gas was mixed with a reactant in the reactor, the reactant may also need to be absorbed in the electrolytic material before providing a detectable electrical signal. A possible disadvantage of the conductivity detector is that absorption by the electrolytic material takes time, which lengthens the detector's response time. The disadvantage may be exacerbated if both the gas and reactant need to be absorbed. Another possible disadvantage is a limited sensitivity of the detector. Because gas is normally detected indirectly, where the difference in potential of the electrolytic material indicates the type and/or concentration of the gas, there may be a measurement error between the electrolytic material measurement and correlating this to the concentration of gas.

A typical conductivity detector is described in U.S. Pat. No. 4,440,726 to Coulson and shown in FIG. 1. Typically, an electrolyte, reactant gas, and gas exiting from the column enter the capillary. Electrodes 24 and 28 are normally placed in the electrolyte solution to measure the difference in potential.

Similar to the conductivity detector, the mass spectrometer and other detection systems of gas chromatography have potentially limiting abilities to detect gas with a high degree of sensitivity. As mentioned in U.S. Pat. No. 6,165,251 to Lemieux et al., detection systems in general have insufficient sensitivity to measure amounts of volatiles in the parts per billion concentration range.

Some gas components may have difficulty being detected by the detector, in which case a reactor may be provided to oxidize and/or reduce the gas sample prior to entering the detector. Generally, the reactor heats the gas sample with a reactant to form a detectable compound. The more completely a gas sample is oxidized and/or reduced, the more likely an accurate concentration of a desired gas component is detected by the detector. Partially oxidizing or reducing the gas sample, and the gas component, may still result in the desired component being detected but may not result in an accurate concentration determination of the desired component. The reactant may be a gas, liquid, or solid and varies according to the desired gas to be detected. Typical reactants include air, hydrogen, and oxygen. A detectable compound is one that generally provides an electrical signal detectable by the detector.

Although it facilitates detection for some gases, the traditional reactor may not enable sufficient detection or efficient oxidation and/or reduction for other gas components. For example, a reactor that reduces an aromatic compound without oxidation typically has difficulty reacting hydrogen with the desired element, such as sulfur, of the aromatic compound. However, oxidizing the aromatic compound is believed to weaken the outer ring structure of the aromatic compound, which may facilitate reduction, or reaction between hydrogen and the desired component, such as sulfur. Therefore, oxidation and reduction may provide a more efficient conversion of the sulfur in the aromatic compound to a detectable component.

Therefore, to provide both oxidation and reduction capabilities to traditional detection systems, two reactors would typically be used, where one reactor may be designated for reducing the gas and the other reactor may be designated for oxidizing the gas.

GB 1,382,640 to Deschamps ("Deschamps") relates to a method that may oxidize a gas sample in the presence of a catalyst to possibly provide an efficient conversion of sulfur compounds to sulfur dioxide at relatively low temperatures. The invention does not typically relate to efficient conversion during oxidation and reduction.

U.S. Pat. No. 6,309,612 to Balachandran et al. ("Balachandran") discloses a ceramic membrane reactor which may contact two reactant gases at different pressures. Balachandran discloses that the two reactant gases may be introduced during o7xidation but the invention does not typically relate to a reactor having the capability to oxidize and/or reduce a gas.

U.S. Pat. No. 6,355,150 to Savin-Poncet et al. ("Savin") discloses a device that may regulate air injected into a reactor for oxidizing hydrogen disulfide to sulfur. However, the invention does not typically relate to a system that has the capability to oxidize and/or reduce a gas.

U.S. Pat. No. 3,934,193 to Hall ("Hall") discloses a conductivity detector for detecting a gas. Hall includes an invention that may, as shown in FIGS. 8 and 9 and described in col. 8, provide a detector that is capable of operating in the reductive and oxidative modes. Hall may also describe the furnace operating at 820° C. in the reductive mode and 840° C. in the oxidative mode with either hydrogen or oxygen as a reaction gas. However, Hall appears to operate the furnace in either the reductive mode or the oxidative mode and not both. Hence, Hall does not typically describe or show a furnace having the capability of reducing and/or oxidizing a gas sample. In fact, Hall represents the traditional reactor where two reactors may be needed to reduce and oxidize the gas sample.

A possible disadvantage of Deschamps, Balachandran, Savin, and Hall is that two reactors are needed to oxidize and reduce a gas. Another possible disadvantage is that these references may require a catalyst for carrying out the oxidation/reduction.

U.S. Pat. No. 5,985,673 to Bao et al. ("Bao") appears to relate to a pyrolyzer which may convert sulfur-containing molecules in a gas sample to hydrogen sulfide by oxidizing the gas sample with oxygen and then reducing the gas sample with hydrogen. However, as shown in the prior art represented by FIG. 1, the pyrolyzer may use a gas chromatograph detector, which typically has limited sensitivity, as described above. In addition, Bao typically introduces the two reactants into the gas sample without either premixing the reactants or homogenously mixing the reactants and gas sample, both of which may enhance detection because the desirous gas component may then be detectable in any part of the gas sample.

What is desired, therefore, is an improved reactor that facilitates detection of a gas sample. What is also desired is a reactor having the ability to efficiently oxidize and/or reduce a gas. Another desire is to provide a detection system having improved sensitivity and reduced response time for detecting a gas component.

SUMMARY OF THE INVENTION

It is, therefore, an object of the invention to provide a reactor having oxidation and/or reduction capabilities for oxidizing and/or reducing a gas sample to facilitate detection.

It is another object of the invention to provide an electrochemical gas sensor coupled to the reactor for improving detection of a gas component exiting the reactor.

These and other objects of the invention are achieved by a reactor having a heater, a passage for transporting a reactant, and a chamber containing a gas sample and being coupled to the passage for receiving the reactant and mixing the reactant with the gas sample.

The reactor further includes a connector leading from the chamber to the heater for transporting a mixture of the reactant and gas sample, and wherein the heater heats the mixture of the reactant and gas sample.

In some embodiments, the reactor may further include a second passage coupled to the connector for transporting a second reactant to the mixture of the reactant and gas sample. The connector may be placed within the second passage and coupled to an outlet, where an electrochemical gas sensor is coupled to the outlet for detecting a gas component in the gas sample.

The electrochemical gas sensor includes a substrate having a substrate, an electrode deposited on a surface of the substrate, an ionomer membrane in contact with the surface and electrode, the ionomer membrane having a first surface and a second surface, and an opening in the ionomer membrane extending from the first surface to the second surface in a location proximate to the electrode, thereby defining a passage for providing diffusion control for the gas.

In another embodiment, the reactor includes a heater, a first passage for transporting a first reactant, a second passage for transporting a second reactant, a connector containing a gas sample and being coupled to the first passage for receiving the first reactant and mixing the first reactant with the gas sample, and where the connector extending from the first passage through the heater and coupling to the second passage for receiving the second reactant and mixing the first reactant and gas sample with the second reactant.

The connector is coupled to the second passage on a side of the heater opposite to the side where the connecter is coupled to the first passage. The second passage then passes through the heater, whereby the second reactant, first reactant, and gas sample are heated by the heater. An electrochemical gas sensor may also be coupled to the second passage for detecting a gas component in the gas sample.

In another aspect of the invention, a method for providing the reactor in accordance with the invention includes the steps of premixing at least two reactant gases together, combining the premix of the at least two reactant gases with a gas sample, heating the premix and gas sample, and detecting a gas component in the gas sample using an electrochemical gas sensor having a substrate, an electrode deposited on a surface of the substrate, an ionomer membrane in contact with the surface and electrode, the ionomer membrane having a first surface and a second surface, and an opening in the ionomer membrane extending from the first surface to the second surface in a location proximate to the electrode, thereby defining a passage for providing diffusion control for the gas.

The method may further include the step of providing a chamber and homogeneously combining the at least two reactant gases and gas sample in the chamber. The method may also include the step of oxidizing/reducing the premix and gas sample.

In another aspect of the invention, the method for providing the reactor includes the steps of mixing a first reactant gas with a gas sample, heating the mixture of the first reactant gas with the gas sample prior to adding the second reactant gas, and adding a second reactant gas to the first reactant gas and gas sample. The method also includes heating the first reactant gas, second reactant gas, and gas sample together and detecting a gas component in the gas sample using an electrochemical gas sensor having a substrate, an electrode deposited on a surface of the substrate, an ionomer membrane in contact with the surface and electrode, the ionomer membrane having a first surface and a second surface, and an opening in the ionomer membrane extending from the first surface to the second surface in a location proximate to the electrode, thereby defining a passage for providing diffusion control for the gas.

The method may also include the step of providing a chamber and homogeneously combining the first reactant gas, second reactant gas, gas sample, and combinations thereof in the chamber.

DETAILED DESCRIPTION OF THE DRAWINGS

Figure 1:
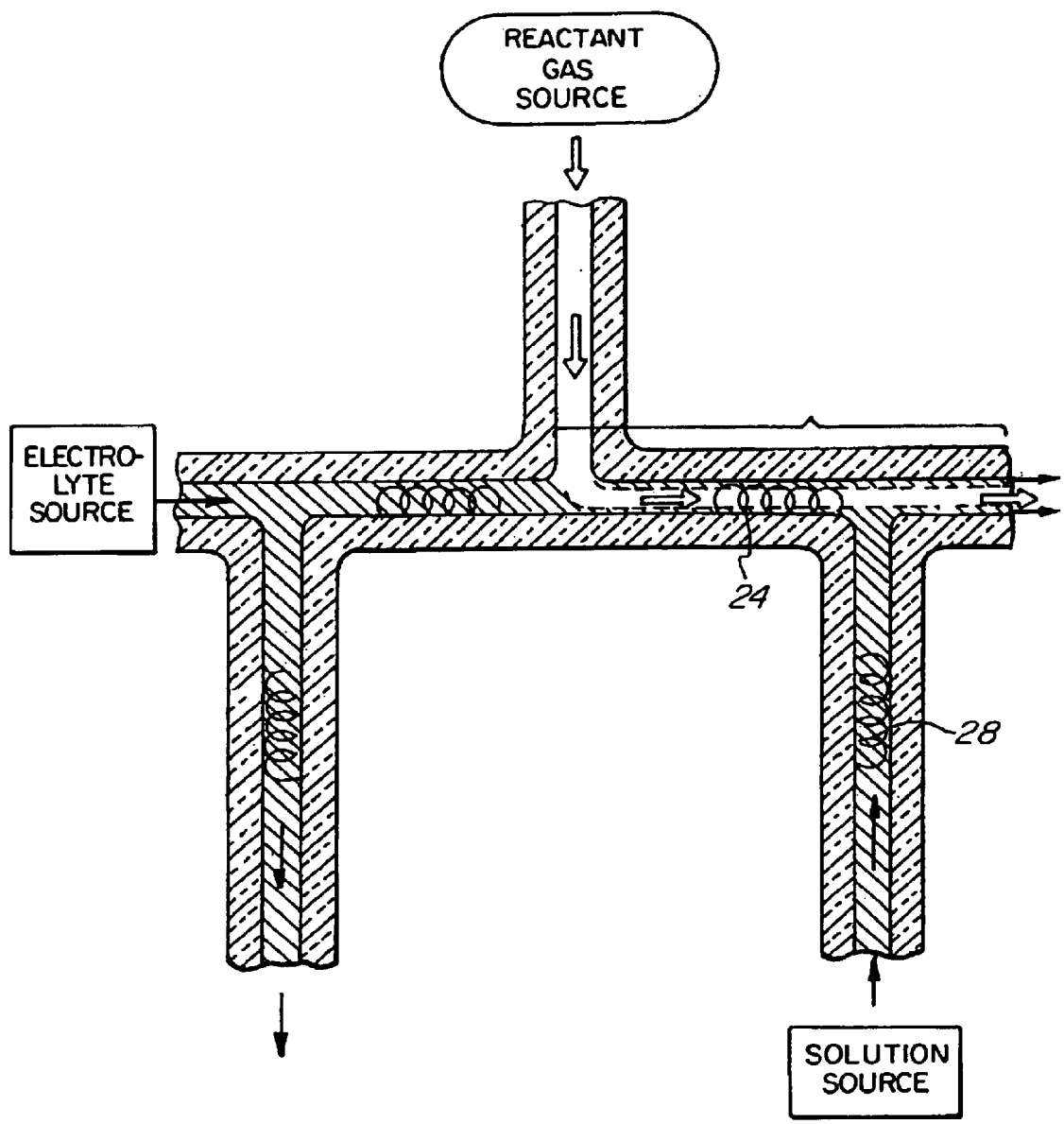
FIG. 1 depicts a conductivity detector known in the prior art.
Figure 2:
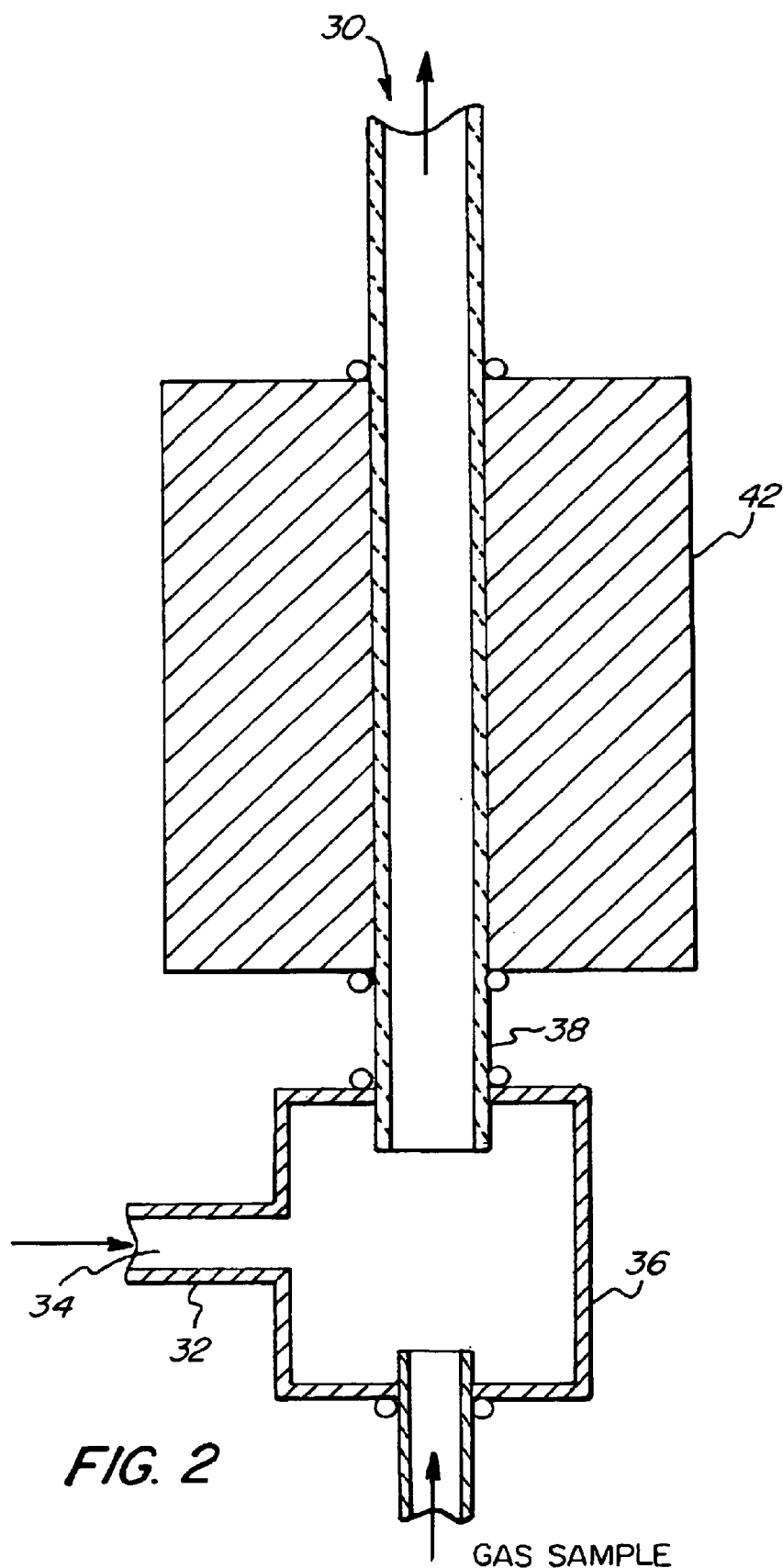
FIG. 2 depicts a reactor in accordance with the invention.

FIG. 2 depicts the reactor 30 in accordance with the invention. Reactor 30 includes a passage 32 for transporting a reactant 34 and a chamber 36 for containing a gas sample which in turn contains a gas component that is ultimately detected by the invention.

Passage 32 may originate from a reactant source, such as an oxygen or hydrogen reservoir, that terminates at chamber 36. Reactant 34 is typically another gas, such as oxygen or hydrogen, that reacts with a gas sample to aid in detecting the desired gas component. Reactant 34 should not be limited to gases but may be any compound or element, in either a solid or liquid state, that facilitates detection of the gas component. Moreover, it should be known that reactant 34 may also be more than one reactant gas, liquid, solid, or combination thereof.

The gas sample, which terminates and mixes with reactant 34 in chamber 36, may have originated from an outlet of a gas chromatograph column. Chamber 36 provides a homogenous mixture of reactant 34, or multiple reactants 34, and gas sample. It should be understood that chamber 36 is desirable but not necessary for reactor 30 to properly operate. Chamber 36 is any containment system coupled to passage 32 that permits reactant 34, or reactants 34, and gas sample to mix together. Chamber 36 need not be air or water tight to function and may be any container of any shape, such as a tube, conduit, another passage, channel, box, and the like.

Reactor 30 further includes connector 38 coupled to and extending from chamber 36 to heater 42 for transporting the mixture of reactant(s) 34 and gas sample. Connector 38 may further extend through heather 42, where reactant(s) 34 and gas sample are heated within connector 38 or connector 38 may terminate prior to heater 42 and where reactant(s) 34 and gas sample are then transported through heater 42 via another conduit. Connector 38 and passage 32 both have the same limitations as each other and may be a tube, conduit, channel, box, and the like.

Figure 3:
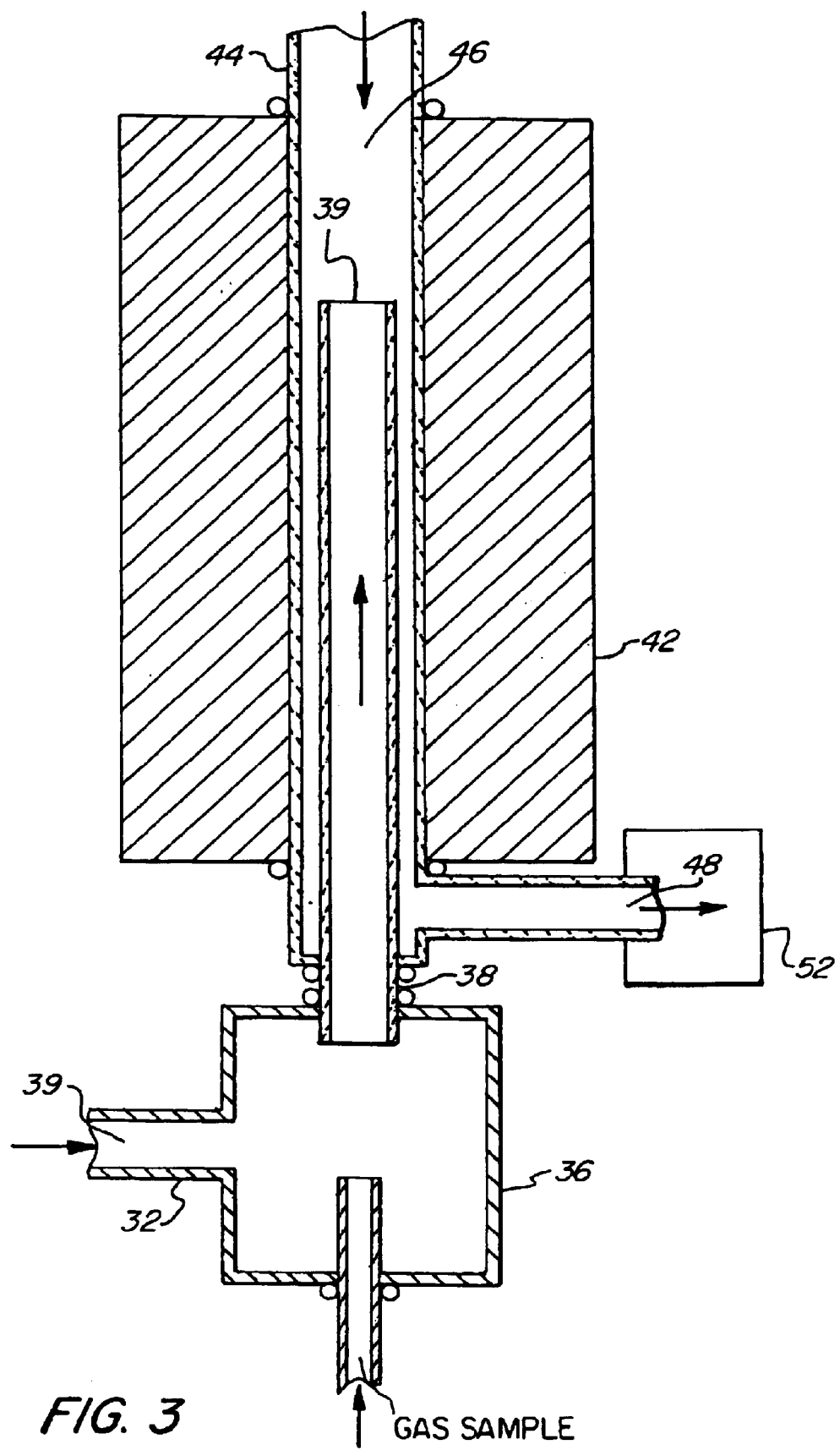
FIG. 3 depicts another embodiment of the reactor shown in FIG. 3.

Heater 42 is any known or novel heating element for heating reactant(s) 34 and/or gas sample and is not germane to the invention In a further embodiment shown in FIG. 3, reactor 30 may also include second passage 44 coupled to connector 38 for transporting a second reactant 46 to the mixture of reactant 34 or reactants 34 and the gas sample. Second passage 44 includes the same limitations as passage 32. Second passage 44 may surround outlet 39 of connector 38, as shown, and direct the emissions of connector 38 back through heater 42 toward outlet 48.

The definition of coupling, as referenced above describing the connections between passage 32, chamber 36, and/or second passage 44, means any direct or indirect connection. Hence, as shown in FIG. 3, passage 32 and connector 38 are coupled to chamber 36, even though one extends to an interior of chamber 38, and second passage 44 is coupled to connector 38, even though there is no contact between them.

Figure 4:
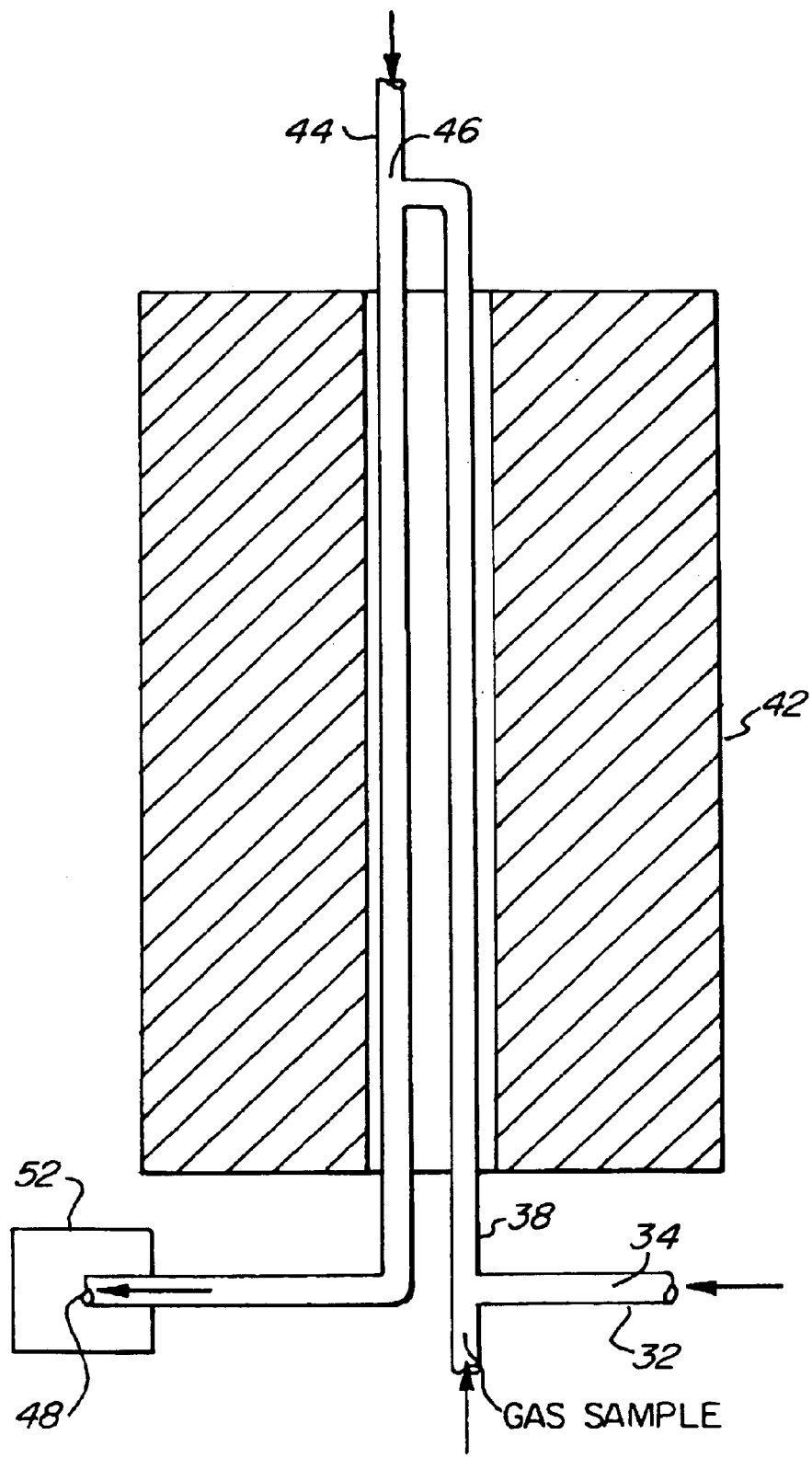
FIG. 4 depicts another embodiment of the reactor shown in FIG. 3.

In another embodiment shown in FIG. 4, connector 38 passes through heater 42 and couples to second passage 44 on the opposite side of heater 42 from where connector 38 joins passage 32 or chamber 36. Although not shown in FIG. 4, chamber 36 may be placed between connector 38 and passage 32.

In some instances, it may be desirable for heater 42 to heat all reactants, 34 and 46, together with the gas sample at the same time and temperature, in which case the embodiment shown in FIG. 2 may be preferred. In other instances, it may be desirable to separate the oxidation and reduction reactions from one another, in which case the embodiment shown in FIGS. 3 and 4 may be preferred.

As shown, after the mixture of reactant 34 and gas sample pass from connector 38 to second passage 44, a second reactant 46 is mixed with reactant 34 and gas sample. Second reactant 46 may be a reactant that facilitates reduction, such as hydrogen.

An advantage of the embodiments shown in FIGS. 3 and 4 over the embodiment shown in FIG. 2 include the ability to separate the oxidation and reduction stages. Separating these stages from one another may reduce interference and increase sensitivity when detecting some elements. For exemplary purposes, the following formulas govern the detection of sulfur in a gaseous mixture, such as a hydrocarbon matrix of propylene.

The oxidation stage involves reactant 34, connector 38, and the gas sample in heater 42

$$C_3H_6 + 4.5O_2 \longrightarrow 3CO_2 + 3H_2O \quad (1)$$

$$CH_3SH + 2.5O_2 \longrightarrow SO_2 + H_2O + CO_2 \quad (2)$$

Where $C_3H_6$ is the propylene and $CH_3SH$ is methyl mercaptan, the compound containing sulfur, where the sulfur is to be detected.

As equation 1 shows, the propylene reacts with the oxygen introduced during oxidation to form $CO_2$ and water. The sulfur compound reacts with the oxygen to form $SO_2$, water, and $CO_2$.

The reduction stage involves second reactant 46, second passage 44, and the gas sample in heater 42.

$$SO_2 + H_2 \longrightarrow H_2S + O_2 \quad (3)$$

$$H_2 + 0.5O_2 \longrightarrow H_2O \quad (4)$$

$SO_2$ reacts with the hydrogen introduced during reduction to form $H_2S$ and oxygen and the remaining hydrogen and oxygen react to form water. $H_2S$ is detected by sensor 52 to indicate the amount of sulfur present in the propylene.

It is understood that equations 1 through 4 depend upon temperature and pressure within reactor 42. For exemplary purposes, the temperature is 1000° C. and the pressure is 1 atm. However, any temperature or pressure may be used provided the equations are modified accordingly and that the temperature and pressure are not germane to the invention. Although sensor 52 may detect $SO_2$, which would also indicate the amount of sulfur, empirical or theoretical information shows that the sensor is more sensitive to $H_2S$ and, therefore, more easily detected by sensor 52 and more accurately indicates the amount of sulfur present.

By way of comparison, in the embodiment shown in FIG. 2, oxidation and reduction occurs simultaneously and results in a loss in sensor sensitivity. For the same sulfur compound methyl mercaptan in propylene, hydrogen reacts with the oxygen of equation 1 to form water. Therefore, not all of the oxygen in equation 1 can be used to convert propylene to $CO_2$, which results in the formation of carbon, or C, instead of $CO_2$. Coke, or carbon, then builds up within reactor 42 and is known to absorb $H_2S$. Hence, detecting an accurate amount of sulfur in propylene $H_2S$ is hindered because part of the $H_2S$ is absorbed and undetectable. In other words, hydrogen may be argued to interfere with the conversion of propylene to $CO_2$ in embodiments where the oxidation and reduction stages are not separated. This is more particular described in formula 5.

$$C_3H_6 + 1.5O_2 \longrightarrow 3C + 3H_2O. \tag{5}$$

In another example of detecting a total amount of sulfur in a sulfur compound, such as methyl mercaptan $CH_3SH$, $H_2S$ may be formed and detected without a need to oxidize the compound. For example, $$CH_3SH + H_2 \longrightarrow CH_4 + H_2S \tag{6}$$

In addition to reducing possible interference introduced when oxidation and reduction occur simultaneously, separating the oxidation and reduction stages also results in improved, or more efficient, conversion. For some aromatic ring structured compounds, such as thiophene, it is difficult to reduce the compound because of the outer ring structure of carbon elements, which tend to hinder hydrogen from reacting with the sulfur element inside the ring structure. However, if these aromatic ring structured compounds are first oxidized before being reduced, the oxygen reacts with the carbon elements to form $CO_2$ and $SO_2$, which permits a subsequent introduction of hydrogen in a reduction stage to react with the $SO_2$ to form $H_2S$. As a result, less coke is formed and more sulfur is converted to $H_2S$. This is more particularly shown in the following formulas.

$$C_4H_4S + 5O_2 \longrightarrow SO_2 + YCO_2 + 2H_2O \tag{7}$$

$$SO_2 + H_2 \longrightarrow H_2S + O_2 \tag{8}$$

Where $C_4H_4S$ is thiophene.

It should be known that not all aromatic compounds require both oxidation and reduction, as with thiopene, and that some aromatic compounds may be oxidized or reduced to provide sufficient detection of the desired component. For example, for the detection of Nitrogen in pyridine, reduction is not needed to efficiently convert Nitrogen into nitrous oxide NO, which is detectable by sensor 52.

$$C_5H_5N + \frac{13.5}{2}O_2 \longrightarrow NO + 5CO_2 + \frac{5}{2}H_2O \tag{9}$$

Conversely, for the detection of chlorine in methylene choride, oxidation is not needed to efficiently convert Chlorine into hydochloride HCl, which is detectable by sensor 52.

$$CH_2Cl_2 + 2H_2 \longrightarrow 2HCl + CH_4 \tag{10}$$

For detecting an amount of phosphine present in a phosphorous composition, reduction with hydrogen suffices to efficiently convert the phosphorous compound into phosphine, which is detectable by sensor 52. However, empirical testing shows increasing the temperature within reactor 42 to 1200° C., as opposed to 1000° C. for sulfur, chlorine, or nitrogen measurements, facilitates reduction and, therefore, detection of phosphine, whereas detection of sulfur, chlorine, or nitrogen is not needed to be enhanced at this elevated temperature to facilitate detection. In the alternative, and in some embodiments, placing sodium borohydride within reactor 42 facilitates reduction of the phosphorous compound at a reactor temperature of between approximately 600°–1000° C. The following formula illustrates the conversion from a phosphorous compound to phosphine.

$$(C_6H_5)_3P + 3H_2 \longrightarrow 3C_6H_6 + PH_3 \tag{11}$$

The more efficient the oxidation/reduction, the more likely the electrons released during oxidation/reduction indicate the component to be detected and the more accurate the concentration of the component is determined. A preferred range for oxidizing/reducing the component is to an efficiency of between approximately 90% and approximately 100%. A more preferred range for oxidizing/reducing the component is between approximately 95% and approximately 100%. An even more preferred range for oxidizing/reducing the component is between approximately 98% and approximately 100%. The most preferred is to oxidize/reduce the component to 100% or approximately 100% efficiency. As a result of complete, or efficient, oxidation/reduction, the gas component is detected more accurately than traditional detectors. Traditional detectors generally have detection capabilities in the ppm range, that merely oxidize or reduce or do so with a lesser efficiency, or not as completely, than reactor 30, which generally has detection capabilities in the ppb range.

It is understood that although reactant 34 and second reactant 46 are described to be oxidative and reductive reactants, respectively, in other embodiments, reactant 34 may be reductive and second reactant may be oxidative.

Figure 5:
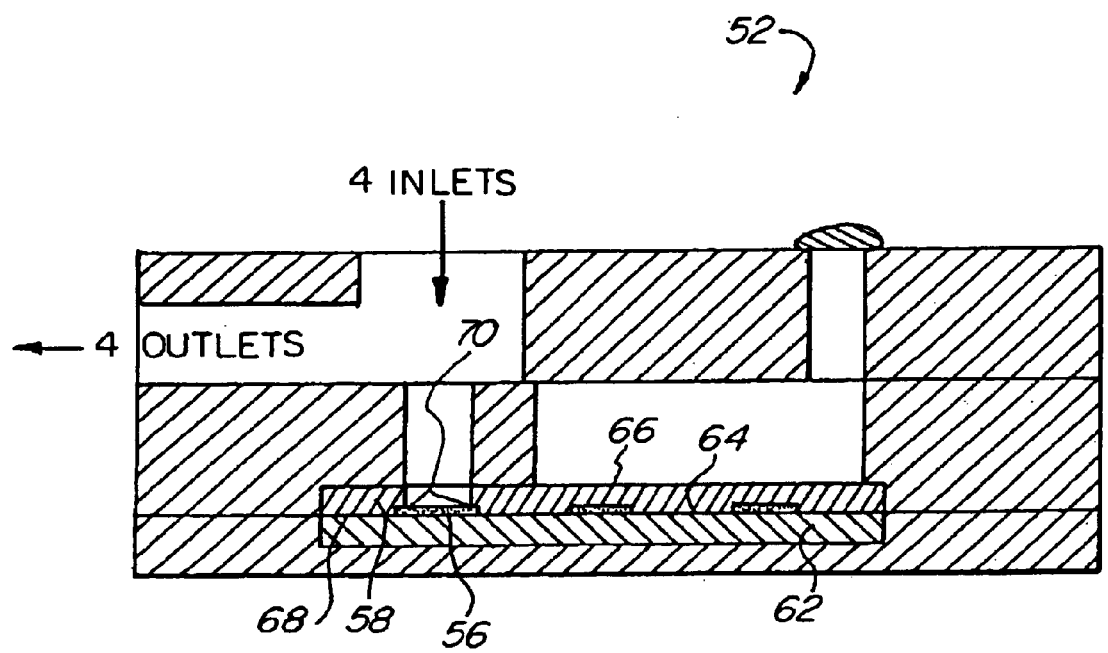
FIG. 5 depicts an electrochemical gas sensor used with any of the rectors shown in FIGS. 2–4.

As shown in FIG. 5, electrochemical gas sensor 52 is placed at an outlet 48 of second passage 44 for detecting a gas component in the gas sample. Sensor 52 may be used with any of the reactors depicts in FIGS. 2–4 having an outlet. Sensor 52 provides enhanced sensitivity over traditional sensors and/or conductivity sensors, the disadvantages of these are mentioned above under the Background of the Invention, due to the 3 way contact between the gas sample to be analyzed, sensing electrode 56, and electrolytic material 58. The 3 way direct contact permits the gas component in the gas sample to be detected without necessitating the gas sample be substantially absorbed or diffused through any electrolytic solution or membrane, thereby reducing the sensor response time and, without possible losses through absorption or diffusion, sensitivity may also be enhanced.

Sensor 52 includes a substrate 62 having a surface 64 for depositing electrodes thereon, an electrode 56 in contact with surface 64, an ionomer membrane 58 in contact with surface 64 and electrode 56, ionomer membrane 58 having a first surface 66 and a second surface 68, and an opening 70 in ionomer membrane 58 extending from first surface 66 to second surface 68 in a location proximate to electrode 56, thereby defining a passage for providing diffusion control for the gas.

In all of the embodiments shown in FIGS. 2–4, and for the purpose of detecting compounds having hydrogen, the presence of oxygen plays a significant role in the oxidation and/or reduction of the gas sample. If there is an insufficient amount of oxygen, oxidation/reduction may be limited, which inhibits a complete oxidation/reduction. An excess amount of oxygen will react with the hydrogen in the compound that is to be detected and such a reaction may lead to the formation of condensation, which, in effect, absorbs the hydrogen in the compound that is to be detected.

For the embodiments shown in FIGS. 2–4, for approximately every 100 cm³ of H₂, the range of oxygen is preferably between approximately 1 and 10 cm³. A more preferable range of oxygen per 100 cm³ of H₂ is between approximately 2 and 6 ft³. A preferred medium for providing oxygen is air because it is in a gas phase as opposed to a liquid phase.

The flow rate of reactants 34 and 36 are dependent upon the size of the gas sample, which may be expressed in volume, and chemical composition of the organic compound. For example, referring to formula 1, for sufficient oxidation of 1 ml of propylene, 4.5 ml/min of oxygen or its equivalent of 21.42 ml/min of air is needed. The saturated water vapor pressure at 25° C., above which undesirably leads to water condensation, is 23.756 mm of mercury, which is 3.12% of atmospheric pressure (23.756 mmHg/760 mmHg×100=3.12%). According to formula 4, 1 ml water needs 0.5 ml of oxygen. Therefore, to avoid water condensation, which leads to h2s absorption and loss in signal at 25° C. and 1 atm, the oxygen content is ½ that of the saturated water vapor pressure, or 1.56%, of the total reaction gas mixture. On this basis, and referring to formula 1, the hydrogen flow rate is either 64.10 (100/1.56) times the oxygen flow rate. Instead of oxygen, air may be used, in which case the hydrogen flowrate is 13.46 times the flow rate of air.

Figure 6:
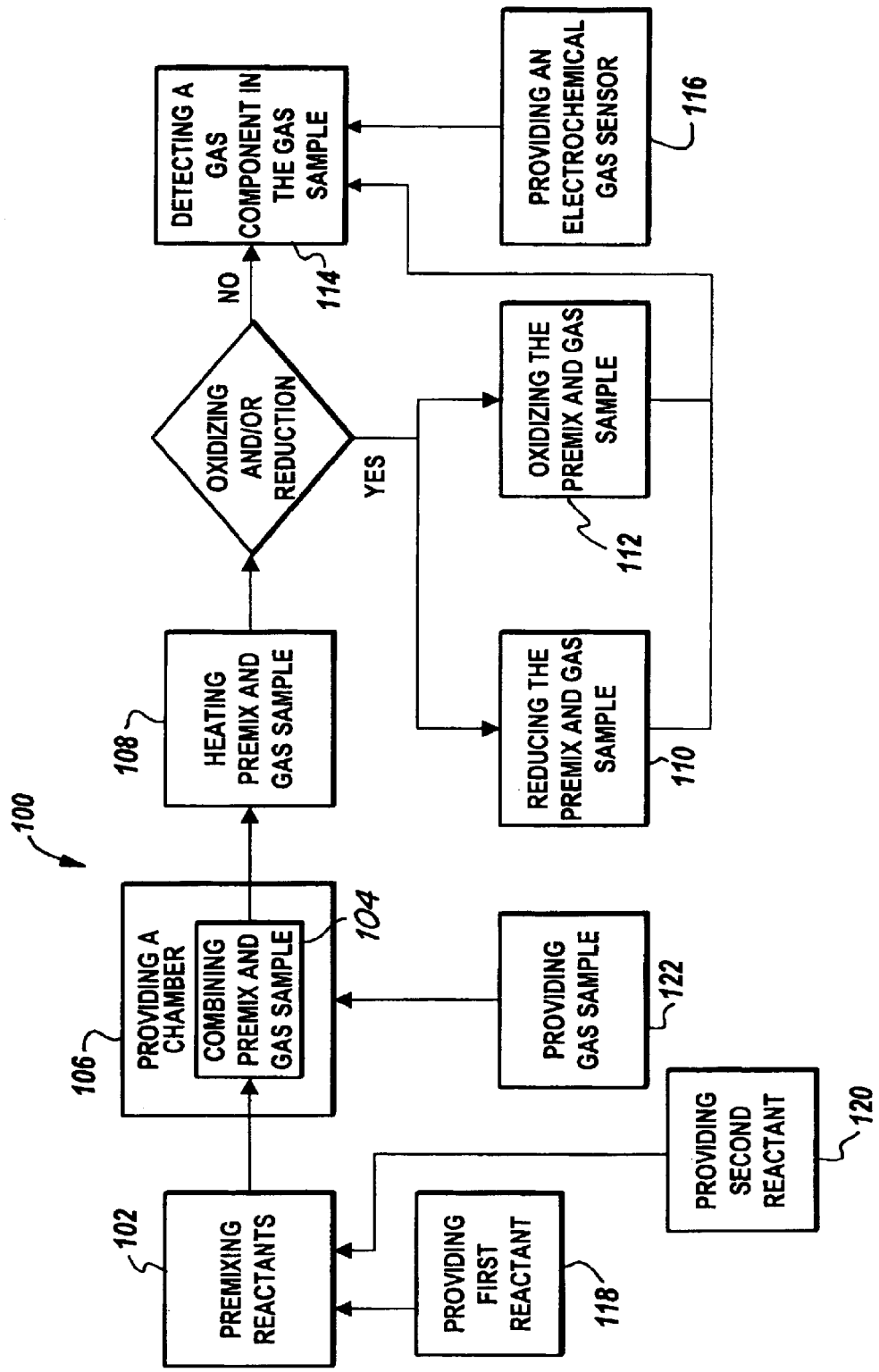
FIG. 6 depicts a method for providing the reactor.

FIG. 6 depicts a method 100 for providing a reactor, including the steps of providing 118 a first reactant, providing 120 a second reactant, and premixing 102 the first and second reactants together. Although only two reactants are shown to be premixed together, method 100 may mix any number of reactants together.

Method 100 further includes the step of providing 122 a gas sample and combining 104 the premix and gas sample together. Optionally, method 100 may also include the step of providing 106 a chamber and homogeneously combining the premix and gas sample in the chamber. Method also heats 108 the premix and gas sample in, preferably, heater 42. Method further provides 116 an electrochemical gas sensor, in accordance with the description of sensor 52, and detects 114 a gas component in the gas sample.

Optionally, and for embodiments where oxidation and/or reduction may be desired for facilitating detection 114 of the gas component, method 100 may include the step of reducing 110 the premix and gas sample. In addition to, or instead of reducing 110 the premix and gas sample, method 100 may also include oxidizing 112 the premix and gas sample. Oxidation and/or reduction include all known or novel manners in the art.

Figure 7:
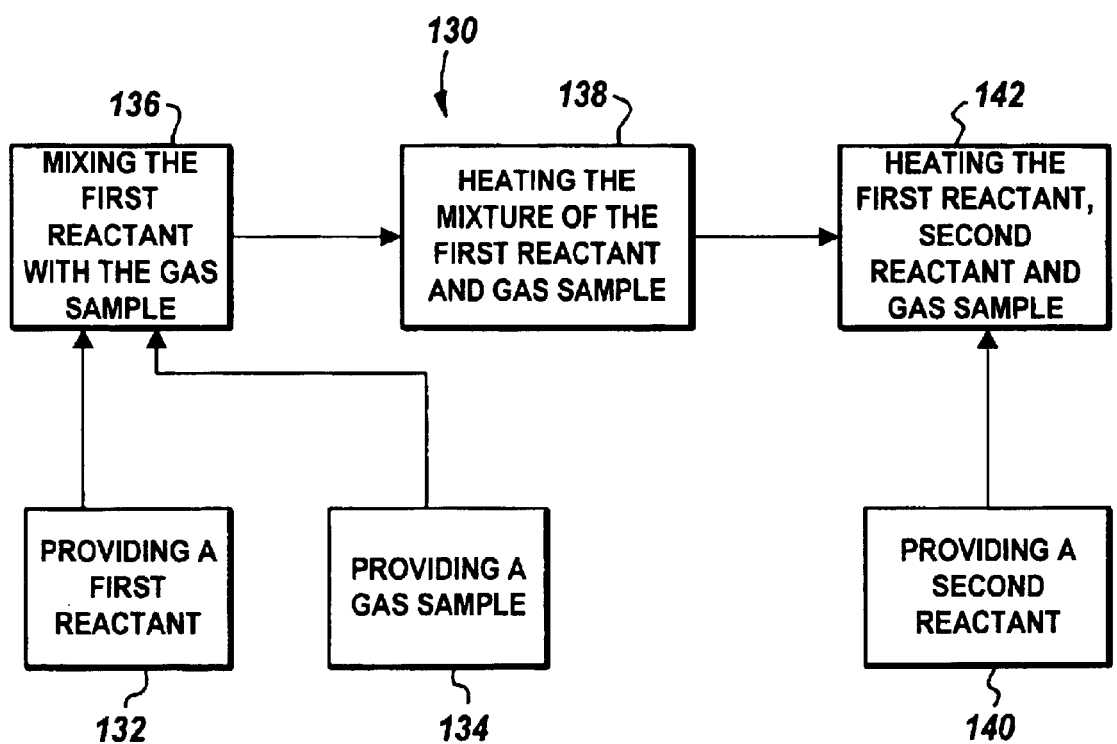
FIG. 7 depicts another aspect of a method for providing the reactor.

In another aspect of the invention, FIG. 7 depicts a method 130 for providing a reactor, including the steps of providing 132 a first reactant, providing 134 a gas sample, and mixing 136 the first reactant with the gas sample. Optionally, method 130 may also include the step of providing a chamber and homogeneously mixing the first reactant and gas sample together in the chamber.

Method further includes heating 138 the mixture of the first reactant and gas sample in, preferably, heater 42. Method further provides 140 a second reactant and heats 142 the first reactant, second reactant, and gas sample together. Method 130 also provides 150 an electrochemical gas sensor, in accordance with the description of sensor 52, and detects 148 a gas component in the gas sample.

Optionally, and for embodiments where oxidation and/or reduction may be desired for facilitating detection 148 of the gas component, method 130 may include the step of reducing 144 the mixture of the first reactant, second reactant, and gas sample. In addition to, or instead of reducing 144 the mixture of the first reactant, second reactant, and gas sample, method 130 may also include oxidizing 146 the first reactant, second reactant, and gas sample. Oxidation and/or reduction include all known or novel manners in the art.

Similar with method 100, although only two reactants are shown in FIG. 7, multiple reactants may be mixed 136 with the gas sample and/or heated 142 with the first reactant and gas sample.

The present invention, therefore, provides a

Although the invention has been described with reference to a particular arrangements of parts, features and the like, these are not intended to exhaust all possible arrangements or features, and indeed many other modifications and variations will be ascertainable to those of skill in the art.

What is claimed is:

1. A reactor, comprising:
   a heater;
   a first passage for transporting a first reactant;
   a second passage for transporting a second reactant;
      a connector leading from said first passage to said heater for transporting a mixture of the first reactant and gas sample contained within said connector;
   said second passage coupled to said connector for transporting the second reactant to the mixture of the first reactant and gas sample;
   said connector is placed within said second passage; and
   wherein said heater heats the mixture of the first reactant and as sample and, subsequently, the mixture of the first reactant, second reactant, and gas sample.

2. The reactor according to claim 1, wherein said second passage is concentric with said connector.

3. The reactor according to claim 1, wherein said connector is coupled to an outlet.

4. The reactor according to claim 3, further comprising a electrochemical gas sensor coupled to an outlet for detecting a gas component in the gas sample.

5. The reactor according to claim 4, wherein said electrochemical gas sensor comprises a substrate having a substrate, an electrode deposited on a surface of the substrate, an ionomer membrane in contact with the surface and electrode, the ionomer membrane having a first surface and a second surface, and an opening in the ionomer membrane extending from the first surface to the second surface in a location proximate to the electrode, thereby defining a passage for providing diffusion control for the gas.

6. A reactor, comprising:
   a heater having a proximal end and a distal end;
   a first passage for transporting a first reactant;
   a second passage for transporting a second reactant;
   a connector containing a gas sample and being coupled to said first passage at said proximal end for receiving the first reactant and mixing the first reactant with the gas sample;
   said connector extending from said proximal end through said eater to said distal end, and coupling to said second passage for receiving the second reactant and mixing the first reactant and gas sample with the second reactant; and
   said second passage passing from said distal end through said heater to said proximal end, whereby the second reactant, first reactant, and gas sample are heated by said heater.

7. The reactor according to claim 6, further comprising a electrochemical gas sensor coupled to said second passage for detecting a gas component in the gas sample.

* * * * *

UNITED STATES PATENT AND TRADEMARK OFFICE
CERTIFICATE OF CORRECTION

PATENT NO. : 6,932,941 B2
DATED : August 23, 2005
INVENTOR(S) : Otto J. Prohaska et al.

It is certified that error appears in the above-identified patent and that said Letters Patent is hereby corrected as shown below:

Column 10,
Line 8, delete "The present invention, therefore, provides a".

Signed and Sealed this

Twenty-second Day of November, 2005

JON W. DUDAS
*Director of the United States Patent and Trademark Office*